United States Patent
Coleman, III

(10) Patent No.: US 7,507,419 B2
(45) Date of Patent: Mar. 24, 2009

(54) **TOPICALLY APPLIED *CLOSTRIDIUM BOTULINUM* TOXIN COMPOSITIONS AND TREATMENT METHODS**

(76) Inventor: William P. Coleman, III, 4425 Conlin St., Metairie, LA (US) 70006

( * ) Notice: Subject to any disclaimer, the term of this patent is extended or adjusted under 35 U.S.C. 154(b) by 0 days.

(21) Appl. No.: 11/483,939

(22) Filed: Jul. 10, 2006

(65) Prior Publication Data

US 2007/0116723 A1    May 24, 2007

Related U.S. Application Data

(62) Division of application No. 10/324,155, filed on Dec. 18, 2002, now abandoned.

(60) Provisional application No. 60/343,389, filed on Dec. 18, 2001.

(51) Int. Cl.
*A61K 39/08* (2006.01)
*A61K 39/02* (2006.01)
*A61Q 15/00* (2006.01)
*A61K 38/00* (2006.01)

(52) U.S. Cl. .................. 424/247.1; 424/65; 424/234.1; 424/236.1; 514/2

(58) Field of Classification Search .................. 424/65, 424/234.1, 236.1, 247.1; 514/2
See application file for complete search history.

(56) References Cited

U.S. PATENT DOCUMENTS

| | | | |
|---|---|---|---|
| 2,952,585 A | 9/1960 | Heller | 424/239.1 |
| 5,670,484 A | 9/1997 | Binder | 514/14 |
| 6,063,768 A * | 5/2000 | First | 514/14 |
| 6,087,327 A | 7/2000 | Pearce et al. | 514/2 |
| 6,113,915 A * | 9/2000 | Aoki et al. | 424/236.1 |
| 6,264,666 B1 * | 7/2001 | Coleman et al. | 606/131 |

FOREIGN PATENT DOCUMENTS

| | | | |
|---|---|---|---|
| DE | 19852981 | * | 5/2000 |
| WO | WO 95/17904 | | 7/1995 |
| WO | WO 03/011333 | | 2/2003 |
| WO | WO 03/026602 | | 4/2003 |

OTHER PUBLICATIONS

Pierard-Franchimont et al. Rev. Med. Liege 54: 846-849, 1999. Original & English translation.*
Hurley HJ. In: Dermatology, (Ed) Moschella SL et al., Third edition, Chapter 59, pp. 1495-1513, 1992.*

* cited by examiner

*Primary Examiner*—S. Devi
(74) *Attorney, Agent, or Firm*—Gavin J. Milczarek-Desai; Quarles & Brady LLP

(57) ABSTRACT

Hyperactive glandular conditions are treated using topically formulated *botulinum* toxin compositions. In the preferred embodiment of the invention, topical *botulinum* preparations are applied directly to the skin by a patient as needed to suppress his or her hyperhidrosis, bromhidrosis, chromhidrosis, nevus sudoriferous, acne, seborrhiec dermatitis or other glandular condition. In other embodiments, topical *botulinum* toxins are applied with the aid of mechanical, electrical, and/or chemical transdermal delivery enhancers.

6 Claims, No Drawings

TOPICALLY APPLIED *CLOSTRIDIUM BOTULINUM* TOXIN COMPOSITIONS AND TREATMENT METHODS

RELATED APPLICATIONS

This application is a divisional application of U.S. patent application Ser. No. 10/324,155, filed on Dec. 18, 2002, now abandoned, which is based on U.S. Provisional Patent Application Ser. No. 60/343,389, filed on Dec. 18, 2001, and entitled "Method and Compositions for Treatment of Hyperhidrosis Using *Clostridium Botulinum* Toxin.

BACKGROUND OF THE INVENTION

1. Field of the Invention

This invention relates generally to the field of medicine. In particular, it relates to methods and compositions that are especially suitable for the treatment of hyperhidrosis, and other conditions of the glands, skin, or smooth and skeletal muscle, and involve the topical application of one or more microbial neurotoxins.

2. Description of the Related Art

Traditionally, bacterial toxins, such as those produced by the genus *Clostridia*, were best known for their wide-ranging pathogenic effects, including food poisoning, tetanus, and botulism. Virulent *botulinum* strains are divided into seven groups, with each group producing an antigenically distinct toxin (the so-called types A-G toxins). While the potency of these toxins differ somewhat (and their physiological modes of action vary), they all result in chemodenervation.

Remarkably, the toxins produced by *Clostridium botulinum* are one of the few large molecules that are absorbed intact from the gastrointestinal tract, where they enter the bloodstream and prevent the contraction of skeletal muscles primarily by inhibiting the release of acetylcholine from nerve cells. One of the more gruesome conditions caused by the ingestion of *C. botulinum* toxin, botulism is a rare but often fatal disease. Symptoms of botulism can include blurred vision, nausea and vomiting, and progressive weakness. Death often results from a gradual paralysis of the muscles required for respiration.

Ironically, it is this "paralytic" property that has led to the development of therapeutic uses for *botulinum* toxin beginning in the 1960's. In fact, *botulinum* toxin is now safely used in the treatment of over a dozen human diseases involving hyperactive skeletal muscles. More generally, pharmaceutical preparations of *botulinum* toxin are used for the treatment of neurological disorders, muscle dystonias, smooth muscle disorders, autonomic nerve disorders, headaches, wrinkles, sports injuries, cerebral palsy, spasms, tremors and pain.

Much recent research has focused on the use of *botulinum* A toxin to block the release of acetylcholine from autonomic nerve endings which control glandular tissue and smooth muscle. This effort has mainly focused on using the toxin to treat hyperhidrosis (excessive sweating) in the axillae and palmar hands. Hyperhidrosis of the palms, soles of the feet, and axillae is caused by excessive episodic sweating from the eccrine glands (as well as the apocrine glands in the axilla). This disorder, which appears to be genetically based, is a cause of great distress for sufferers. It can also be expensive. Aside from the disruption of normal social activities, excessive sweating frequently discolors and thereby ruins clothing.

Traditional therapies for hyperhidrosis include the use of topical aluminum chloride salts such as found in antiperspirants, glutaraldehyde mixtures, anticholinergic drugs, direct excision of affected skin, liposuction and thoracic sympathectomies. All of these therapies have significant drawbacks and are often unsuccessful. Thus, the use of *botulinum* toxins for chemodenervation for hyperhidrosis has gained in popularity over the last several years.

Presently, hyperhidrosis is treated with *botulinum* A, which is commercially produced under the trademark "BOTOX." In a typical treatment regime, BOTOX is injected intradermally in the axilla, palms, and soles with a significant, albeit temporary, effect on reducing sweating. However, intradermal injection-based treatments for hyperhidrosis also have several significant drawbacks.

First, introducing BOTOX through intradermal injections is painful and often involves numerous percutaneous sticks in order to provide relief for the affected area. Moreover, because relief is only temporary, having a medical practioner administer each follow-up injection can be time-consuming, costly, and inconvenient.

Based on these drawbacks for existing treatment options, there remains a need in the art for an effective, long-lasting, and painless treatment for glandular disorders such as hyperhidrosis.

BRIEF SUMMARY OF THE INVENTION

The invention relates in general to compositions and methods for the treatment of hyperactive glandular conditions using topically formulated *Clostridium botulinum* toxins. In one preferred aspect of the invention, topical *botulinum* preparations are applied directly to the skin by a patient as needed to suppress his or her hyperhidrosis. In another aspect, topical *botulinum* toxins are applied with the aid of mechanical, electrical, and/or chemical transdermal delivery enhancers.

The notion that *botulinum* toxin applied topically might be successful for the treatment of hyperhidrosis without injection into the skin represents a new and improved therapy for such glandular disorders. Thus, the present invention substantially departs from existing chemodenervation treatments for excessive sweating, which rely on painful intradermal injections. Moreover, unlike injectable solutions, topical compositions of *botulinum* toxin do not have to be sterile.

A principal objective of this invention is to provide an effective treatment for glandular and smooth muscle disorders without the use of injections.

Another objective of the invention is to provide a new and improved method and compositions for effectively treating other glandular disorders, such as hyperhidrosis, bromhidrosis, chromhidrosis, and nevus sudoriferous.

Another goal of the invention is to provide a method and compositions for the treatment of hyperhidrosis that are painless and easy to apply directly by a patient.

Yet another objective of the invention is to provide topical formulations of *Clostridium botulinum* toxins A-G.

Various other purposes and advantages of the invention will become clear from its description in the specification that follows and from the novel features particularly pointed out therein. Therefore, to the accomplishment of the objectives described above, this invention includes the features hereinafter fully described in the detailed description of the preferred embodiments. However, such description discloses but some of the various ways in which the invention may be practiced.

DESCRIPTION OF THE PREFERRED EMBODIMENT OF THE INVENTION

The present invention features methods for the treatment of maladies of the smooth muscle and sweat glands, such as hyperhidrosis, bromhidrosis, chromhidrosis, and nevus sudoriferous. The invention also includes compositions of topically formulated *botulinum* toxin to be used according to the methods described below for glandular disorders such as excessive oil production.

Three commercial forms of *botulinum* toxin are presently available, including the A toxin ("BOTOX™," Allergan, Inc.; and "DYSPORT™," Ipsen Limited) and the B toxin ("MYOBLOC™," Elan Pharmaceuticals, Inc.). To the best of the applicant's knowledge, the toxins above have been used exclusively in an injectable form. Two reasons for this probably relate to the perception that *botulinum* toxin must enter the muscles to be effective and to the difficulty of passing large molecules across the skin.

Drug penetration is hampered by the relatively low permeability of skin because the barrier properties of the skin allow only for the passage of small, uncharged or polar molecules, such as diatomic oxygen, glycerol, or water. Accordingly, polar molecules larger than water and charged molecules, such as certain amino acids or hydrogen ions, generally do not diffuse across the skin. See Cooper, G. M., The Cell: A Molecular Approach. Chapter 2 "The Chemistry of Cells," p. 81, ASM Press, Washington D.C. (1997). Thus, therapeutically relevant rates of drug delivery often are difficult to achieve by applying a drug to the surface of the body because typical drugs are too large and/or charged to readily diffuse through the skin.

However, the inventor has discovered that *botulinum* toxin treatment by topical application may effectively control hyperactive glandular conditions, such as excessive sweating or malodorous sweating, without the need for injections. While the following explanation is not meant to limit the invention to one mechanism of action, the compositions and methods described herein are thought to act on smooth muscle and glandular targets that are present in the dermis and upper subcutaneous fat of the skin.

Thus, despite the barrier properties of the skin, the large molecular toxins of the invention are surprisingly effective against conditions like hyperhidrosis or bromhidrosis, even when delivered superficially (i.e., to the level of the dermis). Moreover, the toxins of the invention appear to suppress oil gland activity.

Optimally, topical *botulinum* formulations would be water-based as currently available commercial forms of *botulinum* toxin are diluted with, or supplied in, saline. However, other aqueous or non-aqueous delivery carriers, such as creams, lotions, gels, ointments, or emulsions are also contemplated.

For example, 100 units of *botulinum* A may be suspended in a cream vehicle composed of water, mineral oil, propylene glycol, glycerin, cetyl alcohol, methyl paraben and methylcellulose. Similarly, 100 units of *botulinum* B might be suspended in a gel composed of propylene glycol, alcohol, water, and hydroxypropylcellulose. Ideally, these formulations would be of a sufficient volume for a one time treatment of a single axilla or hand. The patient would then simply rub a therapeutically effective amount of the toxin preparation (e.g., covering the affected area with a creme containing 100 units of *botulinum* toxin A) on the affected area as needed to control symptoms.

Under certain conditions, it may be desirable to use chemical agents with the compositions of the invention to enhance penetration through the skin. Such chemical agents may include surfactants, lipids and other aliphatic compounds, liposomes and niosomes. While these compounds increase drug absorption through the skin to some extent, problems with developing pharmaceutically acceptable, stable formulations of both the delivery vehicle and the *botulinum* toxin harbored within can occur.

To help avoid these problems, micro-emulsion formulations of topical agents are preferably used to increase the absorption coefficient over those of conventional "oil and water" emulsion-based creams. See Binks, B. P. *Modern Aspects of Emulsion Science.* Springer-Verlag, 1998 and J. Sjoblom. *Emulsions and Emulsion Stability.* Mareel Dekker, 1996. Such micro-emulsion formulations may be employed to increase drug delivery of the *botulinum* toxin for patients who present exceptional indications. Another compound, hyaluranidase, has been shown to assist drug delivery and would likely also accelerate the absorption of topical *botulinum*.

Other methods of optimizing topical absorption of the toxin include mechanical- or electrical-based transdermal delivery aids. For example, the use of a toxin solution in combination with iontophoretic or electrophoretic devices could be used to enhance penetration through the skin.

It is well known that applying a strong electric field to cells can cause a phenomenon known as electroporation, which actively promotes uptake of drugs through transient cell membrane disruptions caused by the electric field. Thus, *botulinum* toxins A-F may be applied to the skin in the presence of a strong electric field to aid in absorption.

Using iontophoresis, penetration through the skin of ionic drugs can be optimized by using an applied voltage whereby the electrical energy increases the local concentration of the medication at the desired site. Thus, iontophoresis of a charged drug is thought to be accomplished due to simple ion interactions during which the charged drug is repelled from a like-charged portion of the delivery system and attracted to the oppositely-charged portion located at the target for injection.

Mechanical expedients may include delivery of toxins in a water jet. In this embodiment, a high pressure stream of a toxin solution is used to improve penetration into the dermis. For example, the water jet of U.S. Pat. No. 6,264,666 issued to Coleman et al. may be used. The Coleman et al. patent discloses a water spraying device that forces liquid medicants into the epidermis due to the water pressure applied during application. Thus, including an effective amount of one or more *botulinum* toxins in the solution dispensed from a water jet as described would provide an improved way to treat glandular disorders.

The toxins of the invention can also be used to treat acne and seborrheic dermatitis. The inventor has discovered that topical application of BOTOX may lead to a decrease in the activity of the oil glands near the areas of application. Thus, topical application of *botulinum* toxins may also make the skin smoother and less oily. While the following explanation is not meant to limit the invention to one mechanism of action, it is thought that the *botulinum* toxins probably suppress oil gland activity, which is the cause of acne and seborrheic dermatitis.

Furthermore, both for the indication of suppressing sebaceous oil glands and hyperhidrosis, it is thought that the topical *botulinum* enters the skin through pores. Since the penetration of the toxin need only be into the dermis for either of these methods to work, it is conceivable that even large molecules such as *botulinum* toxins could achieve their effects by a "reverse flow" mechanism, which involves the flow of toxin through the pores and into sebaceous, eccrine, and apocrine glands.

The following sample compositions are meant to illustrate a few of the many possible compositions that may be made with *botulinum* toxin. In general, *botulinum* toxins and/or *botulinum* toxin complexes can be obtained from chemical or biological suppliers, such as: List Biological Laboratories, Inc., Campbell, Calif.; Wako of Osaka, Japan; Metabiologics of Madison, Wis. and Sigma Chemicals of St Louis, Mo.

Sample Gel Composition:

| | |
|---|---|
| Botulinum Toxin B | 100 units |
| Hydroxypropylcellulose* | 1.00% |
| Preservative | 0.30% |
| Ethanol (solvent) | 15.00% |
| Antioxidant | 0.05% |
| Water | qs 100% |

*KLUCEL H marketed by Hercules (gelling agent).

The gel is applied with gloves to the affected area as needed.

Sample Cream Composition (oil-in-water emulsion):

| | |
|---|---|
| Botulinum Toxin G | 100 units |
| Glyceryl mono-, distearate | 2.00% |
| Cetyl alcohol | 1.50% |
| Cetylstearyl alcohol/33 EO | 7.00% |
| Polydimethylsiloxane | 1.50% |
| Liquid petroleum jelly | 17.50% |
| Preservative | 0.30% |
| Fragrance | 0.50% |
| Glycerol | 12.50% |
| Water | qs 100% |

The creme is applied to the affected area with gloves to control symptoms as needed.

Various changes in the details, steps and compositions that have been described may be made by those skilled in the art within the principles and scope of the invention herein illustrated and defined. Therefore, while the present invention has been shown and described herein in what is believed to be the most practical and preferred embodiments, it is recognized that departures can be made therefrom within the scope of the invention, which is not to be limited to the details disclosed herein but is to be accorded the full scope of invention so as to embrace any and all equivalent processes and products.

I claim:

1. A method of treating apocrine bromhidrosis in a patient comprising the step of topically applying a therapeutically effective amount of a composition containing a *botulinum* toxin to an area affected by said bromhidrosis in said patient.

2. The method of claim 1, wherein the *botulinum* toxin is selected from the group consisting of *botulinum* toxin types A, B, C, D, E, F, G, and mixtures thereof.

3. The method of claim 1, wherein the *botulinum* toxin is type A.

4. The method of claim 1, wherein said *botulinum* toxin is topically applied with a water jet.

5. The method of claim 1, wherein said *botulinum* toxin is topically applied with a skin-penetration enhancing iontophoretic or electrophoretic device.

6. The method of claim 1, wherein said *botulinum* toxin is topically applied in conjunction with a chemical agent selected from the group consisting of a surfactant, lipid, aliphatic compound, liposome, niosome, micro-emulsion formulation, hylauronidase, and combinations thereof.

* * * * *